United States Patent [19]

Grayzel

[11] Patent Number: 4,796,629

[45] Date of Patent: Jan. 10, 1989

[54] STIFFENED DILATION BALLOON CATHETER DEVICE

[76] Inventor: Joseph Grayzel, 262 Fountain Rd., Englewood, N.J. 07631

[21] Appl. No.: 57,807

[22] Filed: Jun. 3, 1987

[51] Int. Cl.⁴ ............................................ A61M 29/02
[52] U.S. Cl. .................................... 128/344; 604/93
[58] Field of Search ................ 128/1 D, 344; 604/96, 604/103

[56] References Cited

U.S. PATENT DOCUMENTS

| | | | |
|---|---|---|---|
| 2,078,686 | 4/1937 | Rowe | 604/96 |
| 2,435,387 | 2/1948 | Eckard et al. | 128/344 |
| 2,854,983 | 10/1958 | Baskin | 604/105 |
| 3,426,744 | 2/1969 | Ball | 128/344 X |
| 4,018,230 | 4/1977 | Ochiai et al. | 128/344 |
| 4,437,856 | 3/1984 | Valli | 604/29 |
| 4,535,757 | 8/1985 | Webster | 128/1 D |
| 4,637,396 | 1/1987 | Cook | 128/344 |
| 4,702,252 | 10/1987 | Brooks et al. | 604/103 X |

FOREIGN PATENT DOCUMENTS 1327858 8/1973 United Kingdom ................. 604/96

Primary Examiner—Dalton L. Truluck
Attorney, Agent, or Firm—Weingram & Zall

[57] ABSTRACT

The present invention sets forth a balloon catheter device adapted for use with catheters in angioplasty and/or valvuloplasty procedures which is expandable under fluid pressure and incorporates a plurality of stiffening means to resist deformation of isolated portions of the balloon when the balloon is expanded during the treatment procedure. Reinforcing means may also be provided to coact with the stiffening means to strengthen the balloon and/or to assist in the fixing of the location of the stiffening means. Various shapes and tapers of stiffening means can be provided to increase the effectiveness of the stiffening means and/or to reduce the change of damage to the balloon.

26 Claims, 4 Drawing Sheets

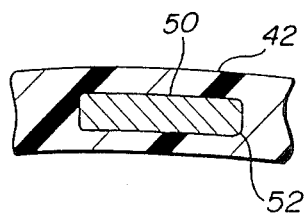
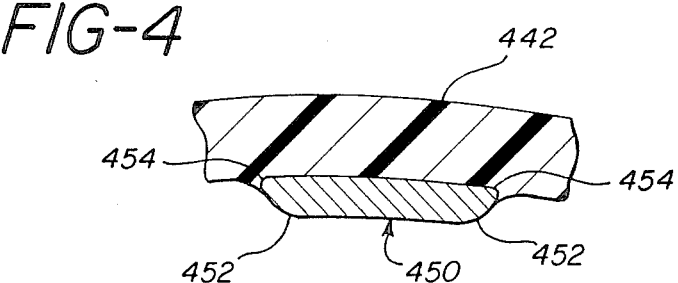
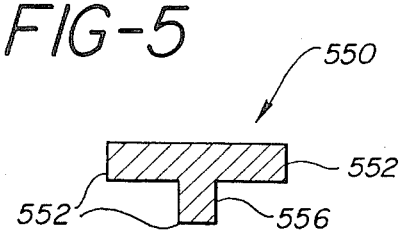
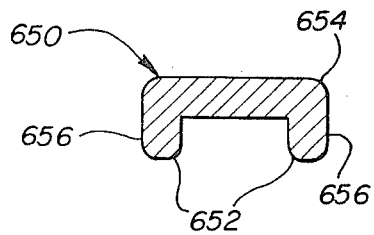
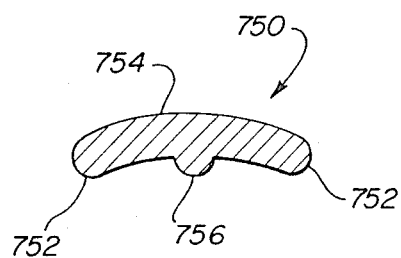

STIFFENED DILATION BALLOON CATHETER DEVICE

BACKGROUND OF THE INVENTION

1. Field of the Invention

This invention relates to balloons for catheter devices adapted to be used for angioplasty and/or valvuloplasty and, more particularly, to balloons having stiffening means to maintain the shape of the balloon when in the expanded state.

2. Description of the Prior Art

Inflatable balloons are presently employed to dilate stenotic arteries (angioplasty) and to dilate stenotic cardiac valves (valvuloplasty). In these procedures, considerable force must be generated to dilate these stenotic arteries and valves, particularly if these arteries and/or valves are heavily ingrown with scar tissue or if they are calcified. Hence, the balloons used for these procedures are filled with liquid under high pressure, often as high as 5 atmospheres (75 p.s.i.).

Despite the use of such high pressures, dilation with these balloons may be less than desired and may not be adequate. One reason for this inadequacy is related to the irregularity of the stenotic structure on which the angioplasty or valvuloplasty procedure is being performed. When the expanded balloon impinges on a local elevation, the elevation will distort the balloon which results in a very limited area of the balloon contacting the local point of irregularity or elevation and thereby greatly reducing the force that can be exerted by the contacting surface of the balloon on the irregular shape. For example, if a local irregularity is one-eighth inch by one-eighth inch at its point of highest elevation, the area of such elevation is one-sixty-fourth square inches. An internal pressure of 75 p.s.i. from the balloon on this area provides a force barely more than one pound. Such a force may be far less than that required to dilate the stenotic orifice of an artery or valve.

Presently this problem is largely unsolved since the ability of balloons to accept higher pressure is compromised by the limitation on the thickness of their skin in order to minimize their bulk so as to enable them to be inserted into the vascular system.

Balloon catheters with stiffeners have been constructed, but they do not address, let alone solve, the problems discussed above. Three patents dealing with stiffened balloons are:

Baskin—U.S. Pat. No. 2,854,983
Valli—U.S. Pat. No. 4,437,856
Rowe—U.S. Pat. No. 2,078,686

Rowe, U.S. Pat. No. 2,078,686, shows a ribbed support surrounded by an inflatable balloon. The ribs do not inflate with the balloon.

Baskin, U.S. Pat. No. 2,854,983, shows a catheter employing an inflatable bag 24. The bag has strips 46 attached thereto. Inflation of the bag serves to "expand" the strips. This serves in turn to keep the area open for drainage. The strips, however, are totally unsuitable and are not intended to augment the stiffness of the contacting surfaces for the expanded balloon, nor to deliver any expansile or dilating forces upon expansion of the balloon.

Valli, U.S. Pat. No. 4,437,856, teaches a dialysis catheter which employs an inflatable portion and a rib structure, which ribs serve as passages for the dialysis fluid, alternatively as collectors for the returning fluid, and alternatively as unperforated supports.

SUMMARY AND OBJECTS OF THE INVENTION

The present invention sets forth a balloon catheter device adapted for use in angioplasty and/or valvuloplasty procedures which is expandable under fluid pressure and incorporates a plurality of stiffening means to resist deformation of isolated portions of the balloon when the balloon is expanded during the treatment procedure. Reinforcing means may also be provided to coact with the stiffening means to strengthen the balloon and/or to assist in the fixing of the location of the stiffening means. Various shapes and tapers of stiffening means can be provided to increase the effectiveness of the stiffening means and/or to reduce the chance of damage to the balloon.

Accordingly, it is an object of the present invention to provide an expandable balloon for use in angioplasty and/or valvuloplasty procedures which incorporates stiffening means to stiffen the surface of the balloon in the expanded state.

A further object of the present invention is to provide an expandable balloon for use in angioplasty and/or valvuloplasty procedures incorporating stiffening means to stiffen the external surface of the balloon in the expanded state which stiffening means are positioned parallel to the axis about which the balloon is expanded.

Another object of the present invention is to provide an expandable balloon for use in angioplasty and/or valvuloplasty procedures which stiffening means greatly augment the force that is brought to bear by the contacting surface of the balloon against irregularities in the surrounding tissue structure.

Yet another object of the present invention is to provide an expandable balloon for use in angioplasty and/or valvuloplasty procedures which incorporates stiffening means to maintain the shape of the external surface of the balloon in the expanded state and which, in addition, incorporates strengthening means associated with the skin of the balloon to increase the pressure tolerance of the balloon and thereby permitting the exertion of great force on the stiffening members to act against irregularities in the surrounding tissue structure.

Still another object of the present invention is to provide an expandable balloon for use in angioplasty and/or valvuloplasty procedures which is relatively resistant to puncture and/or rupture during the procedure.

Another object of the present invention is to provide an expandable balloon for use in angioplasty and/or valvuloplasty procedures which has superior properties for maintaining its shape when in contact with local irregularities in the vessel and/or valve sought to be expanded by the balloon.

A further object of the present invention is to provide an expandable balloon for use in angioplasty and/or valvuloplasty procedures which can be filled with a liquid at higher pressure than other balloons of the same wall thickness.

A further object of the present invention is to provide an expandable balloon for use in angioplasty and/or valvuloplasty procedures which can be constructed with relatively thinner walls to tolerate the same pressures that are used with relatively thicker walled balloons.

Yet another object of the present invention is to provide an expandable balloon for use in angioplasty and/or valvuloplasty procedures which will exert a greater force on objects in contact with the surface of the balloon.

It is yet another object of the present invention to provide an expandable balloon for use in angioplasty and/or valvuloplasty procedures which will be more reliable during use and more predictable in operation.

Yet another object of the present invention is to provide an expandable balloon for use in angioplasty and/or valvuloplasty procedures which is relatively resistant to distortion by contacting surfaces.

It is yet a further object of the present invention to provide an expandable balloon for use in angioplasty and/or valvuloplasty procedures which will produce more accurate expansions of the vessels in which the balloon is expanded.

A further object of the present invention is to provide an expandable balloon for use in angioplasty and/or valvuloplasty procedures which will perform the dilation at a lower pressure and shorter time.

Yet another object of the present invention is to provide an expandable balloon for use in angioplasty and/or valvuloplasty procedures which exerts greater force on local regions of elevation or other irregularities in the structure being treated during its expansion.

It is another object of the present invention to provide an expandable balloon for use in angioplasty and/or valvuloplasty procedures which includes reinforcing means in combination with stiffening means to provide for higher pressure tolerance of the balloon, when expanded, and/or to assist in the positioning of the stiffening means.

A further object of the present invention is to provide an expandable balloon for use in angioplasty and/or valvuloplasty procedures which includes stiffening means, which stiffening means may be of various shapes and tapers in order to enhance the action of the stiffening means.

Yet another object of the present invention is to provide an expandable balloon for use in angioplasty and/or valvuloplasty procedures which includes stiffening means, which stiffening means may be tapered or sized in various shapes to minimize interference with the walls of the balloon during use of the stiffened balloon catheter device.

Other objects and advantages of the invention will be apparent from the following description of the invention, the novel features being particularly pointed out hereinafter in the claims.

BRIEF DESCRIPTION OF THE DRAWINGS

FIG. 3 is a view along lines 3—3 of FIG. 2;

FIG. 4 is another embodiment similar to FIG. 3, showing a stiffening member externally positioned with respect to the skin of the balloon;

FIGS. 5, 6 and 7 show different embodiments of the stiffening members used in the invention;

DETAILED DESCRIPTION OF THE INVENTION

Figure 1:
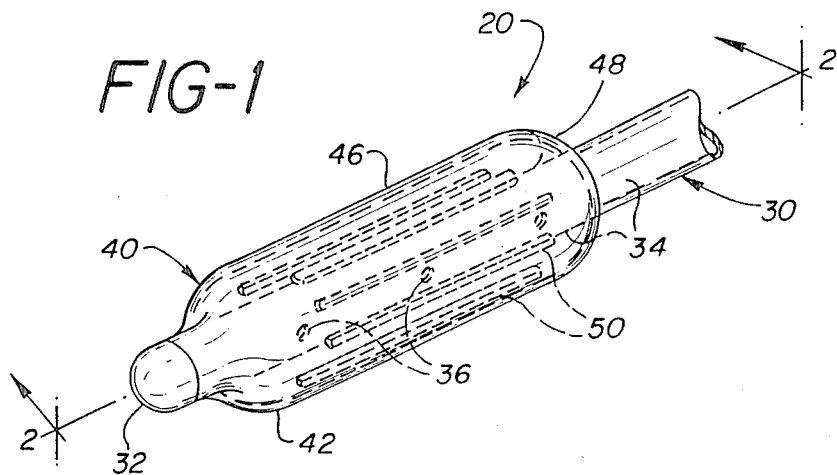
FIG. 1 is a perspective view of a stiffened dilation balloon for angio-valvulo-plasty built in accordance with the teachings of the present invention in the expanded condition.
Figure 2:
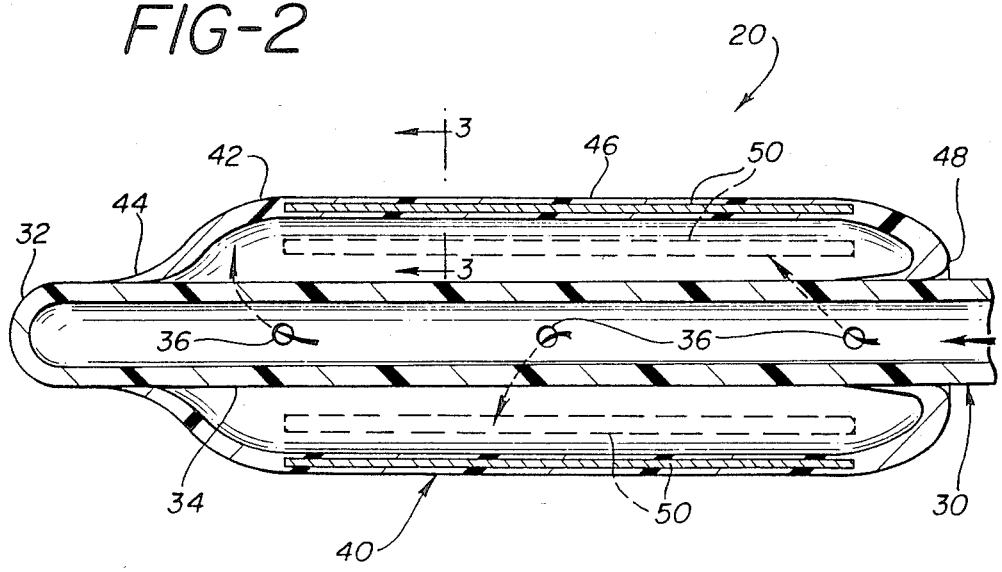
FIG. 2 is a view along lines 2—2 of FIG. 1.

FIGS. 1 and 2 show a perspective view of a dilation balloon associated with a catheter for use in angio-valvulo-plasty procedures, generally indicated at 20. The device consists of a catheter, generally indicated at 30, and an expandable balloon, generally indicated at 40. The catheter 30 has a closed end 32 which is used as a probe for threading the catheter. The catheter could, of course, have a channel formed in it for the placement of a guide wire on which the catheter could travel. The external wall 34 of the catheter has a plurality of passages 36 therein for the passage of pressure fluid into the interior of the balloon 40. The balloon 40 consists of a skin 42 which is connected to the wall of the catheter at a tapered or arcuate front portion 44 and a tapered or arcuate rear section 48.

As seen from FIG. 2, the balloon can be attached to the catheter wall by any convenient bonding method known in the art. For example, at the front section of the balloon 42, the balloon is tapered to a cylindrical section approximating the size of the catheter wall and is bonded to the wall by means of a bonding agent. The rear portion 48 of the balloon shows another method for attaching the balloon to the wall of the wall of the catheter in which the end of the balloon is folded over so as to be inside the expandable chamber. As mentioned, various adhesives or other bonding agents or ultrasonic welding can be used as well as any other wellknown bonding means for attaching the balloon to the catheter section.

The middle portion 46 of the balloon is cylindrical in shape and of relatively uniform and continuous surface. This is the portion of the device which is intended to press upon the stenotic structure to dilate the same by expansion of the balloon. As seen in FIGS. 2 and 3, embedded in the skin 42 of the balloon is a stiffening member 50, which is intended to run the length of the cylindrical section of the balloon or the contacting section of the balloon. This need not necessarily extend from the arcuate front 42 to the arcuate rear 48; but could be shorter. In all likelihood, it would not be longer than the contacting surface, since the stiffening member should be straight in order to minimize the cross-sectional area of the balloon when in the unexpanded or contracted state. The stiffening members 50 have rounded corners 52 so that there will be no sharp edges that would tend to form stress concentration points or initiate rips or stretches in the skin 42 of the catheter device. The skins are usually made from a relatively thin flexible but usually not elastic plastic.

As shown in FIG. 4, it is possible to locate the stiffening member externally of the wall. In this case, a wall 442 of the balloon has a stiffening member 450 attached to one surface. The stiffening member 450 again has rounded upper corners 452 and also a rounded, but wider, bottom surface 454, which contacts the skin 442 of the balloon. The wider bottom surface tends to give a larger surface for adhering of the stiffening member 450 to the skin. The corners, again, are rounded in order to avoid deterioration of the skin by the corners of the stiffening member during the expansion or contraction of the expandable chamber.

In FIG. 4, the stiffening member 450 can be either on the inside or the outside of the skin. The stiffening members when external to the skin can be internally or externally disposed with relation to the envelope of the balloon. The stiffening members can be made from any convenient inert substance from an inert metal to a relatively rigid plastic such as delrin or rynite.

Referring to FIGS. 5, 6 and 7, these are different embodiments of stiffening members that are suitable for use in the stiffened balloon. FIG. 5 is a T-shaped section, generally indicated at 550, having square corners 552 on the sides and the bottom of the T. The purpose of the T leg 556 is to increase the stiffness to the stiffening member with a minimum of cross-sectional area.

Referring to FIG. 6, there is a channel-shaped stiffening member, generally indicated at 650, having rounded external corners 652 at the top surface 654 and the channel legs 656.

FIG. 7 shows a stiffening member similar to FIG. 4, generally indicated at 750, having a curved top 754 to conform to the desired arcuate shape of the external skin of the balloon when the balloon is expanded. The curved surface also adds rigidity to the stiffening member. The external corners 752 are again rounded on the arcuate top 754 and also on the shortened descending leg 756 of the T.

It should be noted that the stiffening members shown in FIGS. 5, 6 and 7 can be mounted on the inside of the skin 442 and possibly embedded in the skin.

Figure 8:
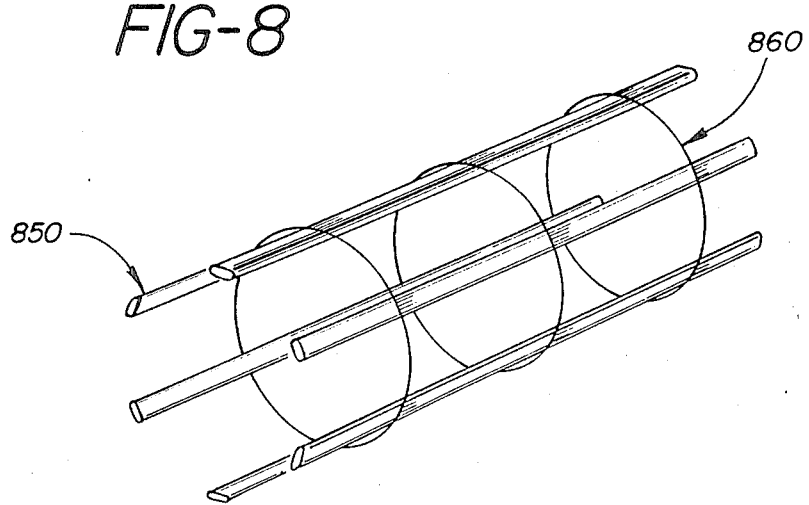
FIG. 8 shows a portion of another embodiment of the invention incorporating strengthening fibers.

FIG. 8 is a partial view similar to a portion of FIG. 2, and shows the wall or skin of the balloon 842 with a series of stiffening members, generally indicated at 850. Running perpendicular or in a generally crosswise or angular direction to the length of the stiffening members are a plurality of strengthening fibers, generally indicated at 860. The fibers can be internally or externally positioned with relation to the skin or embedded or bonded to the wall, and help provide a restraint to the skin so that higher pressures can be transmitted by the pressurizing liquid filling the balloon without ripping or otherwise rupturing the skin. The strengthening fibers can be on the same side or opposite side of the skin from the stiffening members.

Figure 9:
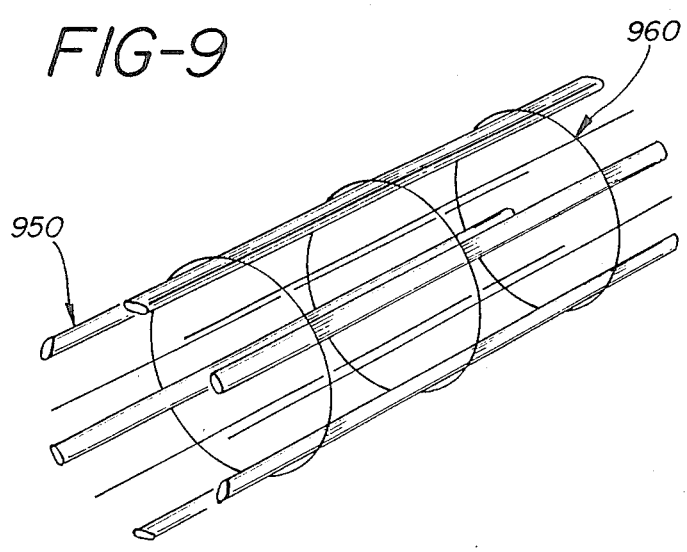
FIG. 9 is another embodiment of the invention incorporating a strengthening mesh.

In FIG. 9, we have an embodiment different from that shown in FIG. 8 in that rather than having a plurality of fibers positioned at an angle to the axis or length of the stiffening members, we have a mesh of fabric which is adapted to coact with the skin of the balloon either externally or internally, or which could also be embedded in the skin to add strength to the skin so that the balloon can hold a liquid maintained at a greater pressure and thereby exert a greater force on the structure being treated the dilating procedure.

The mesh may be on the same side as the stiffening members or on the opposite side.

Figure 10:
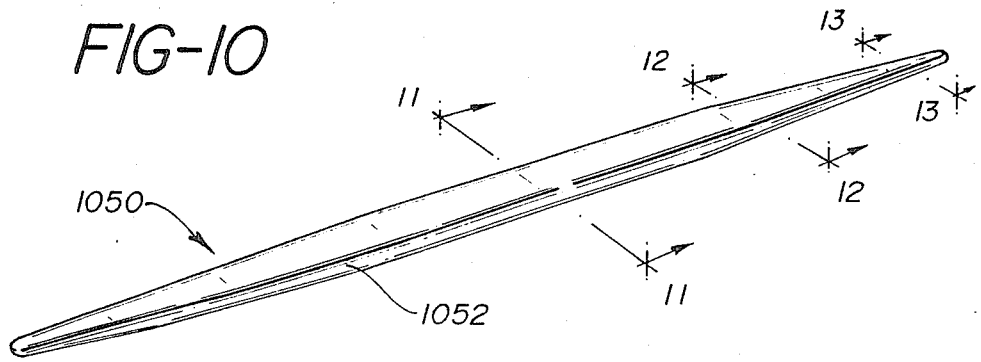
FIG. 10 is a perspective view of a tapered stiffening member of generally rectangular cross-section for use in the present invention.
Figure 14:
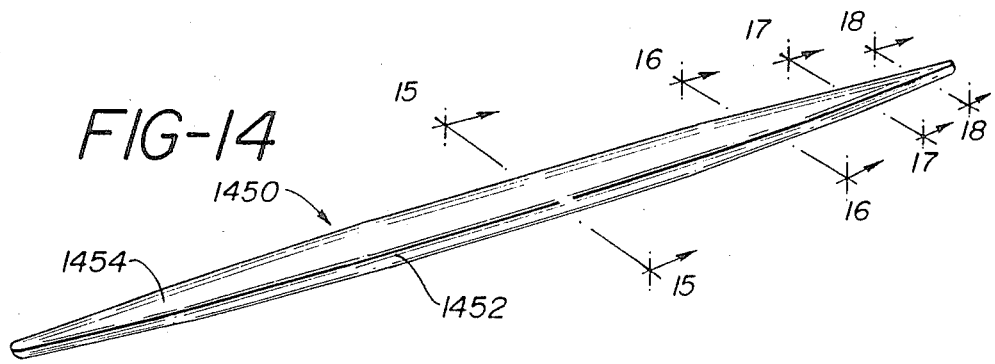
FIG. 14 is a perspective view of a stiffening member for use in the present invention having a stiffening rib to form a T-shape in the central portion of the stiffening member.
Figure 15:
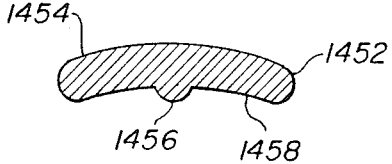
FIG. 15 is a view taken along line 15—15 of FIG. 14.
Figure 17:
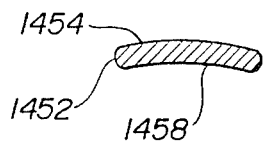
FIG. 17 is a view taken along line 17—17 of FIG. 14.
Figure 16:
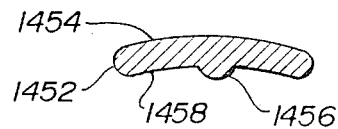
FIG. 16 is a view taken along line 16—16 of FIG. 14 showing a diminution of the stiffening rib.
Figure 18:
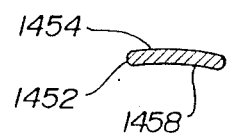
FIG. 18 is a view taken along line 18—18 of FIG. 14.

FIGS. 10 and 14 show perspective views of stiffening members which are tapered.

Figure 11:
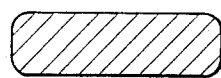
FIG. 11 is a view taken along line 11—11 of FIG. 10.
Figure 12:
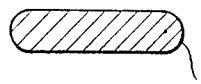
FIG. 12 is a view taken along line 12—12 of FIG. 10.
Figure 13:
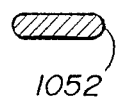
FIG. 13 is a view taken along line 13—13 of FIG. 10.

FIG. 10 shows a stiffening member, generally designated as 1050, is rectangular in cross-section and has relatively parallel edges in the central portion of the stiffening member which is intended to make contact with the wall of the vessel being treated. The stiffening member tapers both in the width and thickness towards either end as shown in FIGS. 11, 12 and 13. The edges 1052 are rounded to minimize the likelihood of damage to the material forming the balloon during the expansion of the balloon or while the balloon is in its collapsed state.

The tapering of the ends of the stiffening member, as shown at 12 and 13, reduces the trauma on the balloon as the balloon moves from its central cylindrical shape towards the end of the balloon where it tapers down to be joined with the wall of the catheter. By having the ends of the stiffening members tapered, they are less rigid and therefore more able to conform to the shape of the balloon at the end of the stiffener thereby reducing the discontinuity of stiffness and/or flexibility between the stiffener and the skin of the balloon.

FIG. 14 and associated FIGS. 15, 16, 17 and 18 show a stiffening member similar to that shown in FIG. 7 but tapered in much the manner as that shown in FIG. 10. Here the stiffening member, generally indicated at 1450, has a T-leg 1456 which extends downwardly in the central portion of the catheter. The top portion 1454 is curved and parallel to the bottom section and the edges 1452 are rounded as those in FIG. 7. As you move from the central or contacting portion of the catheter towards either end, the stiffening member tapers in thickness and in width in the same manner as that discussed in FIG. 10 and its associated Figures. Accordingly, the stiffening T-member 1456 will taper into the bottom of the bottom surface 1458 of the stiffening member and then the stiffening member will taper in thickness and width as it goes towards the ends. The purpose of the tapering is similar to that discussed with respect to FIG. 10.

It can be seen from the above that the use of the stiffening members will, in effect, amplify the force that will be exerted by the balloon on any surface irregularities in the structure being treated. By having a relatively stiff contacting surface, the force exerted by the balloon's contacting surface on the irregularity will be greater and therefore the force will be amplified. Additionally, since the balloon is less deformable, there will be less of a tendency for the areas of the balloon to expand in those regions beyond the anatomic narrowing being treated, which remote expansion, in effect, minimizes the pressure internal to the balloon.

Further, because the external surface of the expanded balloon is stiffer, there is a greater tendency for the re-molded structure to conform to the predetermined cross-sectional configuration of the balloon.

Additionally, as mentioned, since greater pressures can be tolerated in a balloon of the present invention, a greater force can be applied against local irregularities during the dilation procedure to crack or otherwise remold the irregularities which are present.

While several embodiments of the invention have been illustrated and described, it is apparent that many other variations that may be made in the particular design and configuration without departing from the scope of the invention as set forth in the appended claims.

What is claimed is:

1. A balloon catheter for use in angioplasty and/or valvuloplasty procedures comprising:
   a catheter section having a flow passage for pressurized liquid;
   an expandable chamber connected to the catheter section having a wall for containing a pressurized liquid;
   passage means in said catheter section communicating said flow passage with said expandable chamber;
   said expandable chamber having a wall section forming a cylindrical section when expanded;
   a plurality of relatively rigid stiffening members peripherally disposed and axially extending along said expandable chamber, said stiffening members connected along the length thereof to the wall of said expandable chamber and movable with the wall of the expandable chamber; and
   said stiffening members acting to maintain said cylindrical section to resist localized deformation in the surface of the expandable chamber.

2. The device of claim 1 wherein the stiffening members are embedded in the wall of the expandable chamber.

3. The device of claim 1 wherein the stiffening members are disposed on the outside of the wall of the expandable chamber.

4. The device of claim 1 wherein the stiffening members are disposed inside the wall of the expandable chamber.

5. The device of claim 1 wherein the stiffening member has a generally rectangular cross-section; and the corners of the rectangular cross-section are rounded to prevent damage to the wall of the expandable chamber.

6. The device of claim 1 wherein the stiffening member has at least one element perpendicular to another element.

7. The device of claim 1 wherein the stiffening member has an arcuate portion in cross-section.

8. The device of claim 7 wherein the arcuate portion of the stiffening member is adjacent the wall of the balloon and is curved to correspond to the arc of the wall of the expandable chamber when expanded.

9. The device of claim 1 wherein the stiffening member is channel-shaped.

10. The device of claim 1 further comprising strengthening fibers in proximate relation to said wall and coacting with said wall to strengthen the wall against expansion by the pressurizing liquid.

11. The device of claim 1 further comprising a strengthening mesh connected to said wall and coacting with said wall to strengthen the wall against expansion by the pressurizing liquid.

12. The device of claim 10 wherein the strengthening fibers are connected to the struts.

13. The device of claim 11 wherein said mesh is connected to said struts.

14. The device of claim 11 wherein said mesh and said struts are on opposite sides of said wall.

15. The device of claim 1 wherein at least one of said plurality of stiffening members connected to the wall of said expandable chamber is tapered towards at least one end.

16. The device of claim 15 wherein at least one of said plurality of stiffening members is tapered in both width and thickness from the middle portion of the stiffening member towards at least one of the ends of said stiffening member.

17. The device of claim 16 wherein at least one of said plurality of stiffening members connected to the wall of said expandable chamber is tapered in both width and thickness in the direction of both ends of said stiffening member.

18. A balloon catheter for use in angioplasty and/or valvuloplasty procedures comprising:
   a catheter section having a flow passage for pressurized liquid;
   an expandable chamber connected to the catheter section having a wall for containing a pressurized liquid;
   passage means in said catheter section communicating said flow passage with said expandable chamber;
   said expandable chamber having a wall section forming a cylindrical section when expanded;
   a plurality of strengthening fibers connected to the wall of said expandable chamber and movable with the wall of the expandable chamber to increase the tolerance of the chamber for pressurized liquid to expand the chamber;
   a plurality of relatively rigid stiffening members peripherally disposed and axially extending along said expandable chamber, said stiffening members connected along the length thereof to the wall of said expandable chamber and movable with the wall of the expandable chamber; and
   said stiffening members acting to maintain said cylindrical section to resist localized deformation in the surface of the expandable chamber.

19. A balloon catheter for use in angioplasty and/or valvuloplasty procedures comprising:
   a catheter section having a flow passage for pressurized liquid;
   an expandable chamber connected to the catheter section having a wall for containing a pressurized liquid;
   passage means in said catheter section communicating said flow passage with said expandable chamber;
   said expandable chamber having a wall section forming a cylindrical section when expanded;
   a strengthening mesh connected to the wall of said expandable chamber and movable with the wall of the expandable chamber to increase the tolerance of the chamber for pressurized liquid to expand the chamber;
   a plurality of relatively rigid stiffening members peripherally disposed and axially extending along said expandable chamber, said stiffening members connected along the length thereof to the wall of said expandable chamber and movable with the wall of the expandable chamber; and
   said stiffening members acting to maintain said cylindrical section to resist localized deformation in the surface of the expandable chamber.

20. A balloon catheter for use in angioplasty and/or valvuloplasty procedures comprising:
   a catheter section having a flow passage for pressurized liquid;
   an expandable chamber connected to the catheter section having a wall for containing a pressurized liquid;

passage means in said catheter section communicating said flow passage with said expandable chamber;

said expandable chamber having a wall section forming a cylindrical section when expanded;

a plurality of rigid stiffening members peripherally disposed and axially extending along said expandable chamber, said stiffening members connected along the length thereof to the wall of said expandable chamber disposed in parallel array and movable with the wall of the expandable chamber;

a plurality of strengthening fibers connected to the wall of said expandable chamber and movable with the wall of the expandable chamber to increase the tolerance of the chamber for pressurized liquid to expand the chamber; and said stiffening members acting to maintain said cylindrical section to resist localized deformation in the surface of the expandable chamber.

21. A balloon catheter for use in angioplasty and/or valvuloplasty procedures comprising:

a catheter section having a flow passage for pressurized liquid;

an expandable chamber connected to the catheter section having a wall for containing a pressurized liquid;

passage means in said catheter section communicating said flow passage with said expandable chamber;

said expandable chamber having a wall section forming a cylindrical section when expanded;

a plurality of rigid stiffening members peripherally disposed and axially extending along said expandable chamber, said stiffening members connected along the length thereof to the wall of said expandable chamber disposed in parallel array and movable with the wall of the expandable chamber;

a strengthening mesh connected to the wall of said expandable chamber and movable with the wall of the expandable chamber to increase the tolerance of the chamber for pressurized liquid to expand the chamber; and said stiffening members acting to maintain said cylindrical section to resist localized deformation in the surface of the expandable chamber.

22. The device of claim 20 wherein said plurality of strengthening members connected to the wall of said expandable chamber comprise oblong members having a relatively rectangular cross-section configuration, said cross-section configuration tapering in width and thickness towards either end of said strengthening member.

23. The device of claim 20 wherein said plurality of stiffening members connected to the wall of said expandable chamber has at least one element perpendicular to another element in cross-sectional configuration and taper in both width and thickness towards the end of each chamber.

24. The device of claim 21 where said plurality of stiffening members connected to the wall of said expandable chamber comprise oblong members having a relatively rectangular cross-section configuration, said cross-section configuration tapering in width and thickness towards either end of said stiffening member.

25. The device of claim 21 wherein said plurality of stiffening members connected to the wall of said expandable chamber has at least one element perpendicular to another element in cross-sectional configuration and taper in both width and thickness towards the end of each chamber.

26. A balloon catheter for use in angioplasty and/or valvuloplasty procedures comprising:

a catheter section having a flow passage for pressurized liquid;

an expandable chamber connected to the catheter section having a wall for containing a pressurized liquid;

passage means in said catheter section communicating said flow passage with said expandable chamber;

said expandable chamber having a wall section forming an axially straight-walled tubular section when expanded;

a plurality of relatively rigid stiffening members peripherally disposed and axially extending along said expandable chamber, said stiffening members connected along the length thereof to the wall of said expandable chamber and movable with the wall of the expandable chamber; and said stiffening members acting to maintain said axially straight-walled tubular section to resist localized deformation in the surface of the expandable chamber.

* * * * *